United States Patent [19]
Lovitt

[11] Patent Number: 5,097,540
[45] Date of Patent: * Mar. 24, 1992

[54] SELF-CONTAINED HAND-HELD BIDET

[76] Inventor: Harold B. Lovitt, 8427 Kirkwood Dr., Los Angeles, Calif. 90046

[*] Notice: The portion of the term of this patent subsequent to Jan. 2, 2007 has been disclaimed.

[21] Appl. No.: 444,465

[22] Filed: Dec. 1, 1989

Related U.S. Application Data

[63] Continuation-in-part of Ser. No. 249,053, Sep. 26, 1988, Pat. No. 4,890,340.

[51] Int. Cl.⁵ .................. A61H 35/00; A61H 9/00
[52] U.S. Cl. ............................. 4/443; 4/448; 128/66
[58] Field of Search ............ 4/420, 420.1, 420.2, 4/420.3, 420.4, 420.5, 443, 444, 445, 446, 447, 448; D23/295, 299; D24/60; 128/66, 200.14–200.20; 604/279, 58, 60, 217, 218, 212, 185, 37, 39, 41, 240, 36–38, 40, 42, 150–152, 156, 183, 187, 310, 311; 222/79, 526, 533, 534, 538, 215, 211, 333

[56] References Cited

U.S. PATENT DOCUMENTS

| | | | |
|---|---|---|---|
| 643,867 | 2/1900 | DeVilbiss | 604/58 |
| 1,056,855 | 3/1913 | Tamagno | 222/534 |
| 1,482,747 | 2/1924 | Howe | 128/66 |
| 1,979,014 | 10/1934 | Schleif | 222/79 |
| 2,208,031 | 7/1940 | Hooper | 604/150 |
| 2,751,116 | 6/1956 | O'Brian | 222/79 |
| 3,104,664 | 9/1963 | Ladd | 604/150 |
| 3,148,806 | 9/1964 | Mohbay | 128/200.23 |
| 3,203,318 | 8/1965 | Black | 222/79 X |
| 3,298,577 | 1/1967 | Chlystun | 222/530 X |
| 3,420,228 | 1/1969 | Kalbfeld | 128/66 |
| 3,476,111 | 11/1969 | Matheson | 222/530 |
| 3,653,377 | 4/1972 | Rebold | 128/66 |
| 3,703,170 | 11/1972 | Ryckman, Jr. | 128/66 |
| 3,731,676 | 5/1973 | Rebold | 128/66 |
| 3,783,867 | 1/1974 | Summersby et al. | 128/66 |
| 3,800,786 | 4/1974 | Kovach | 128/66 |
| 3,808,608 | 5/1974 | Caplan | 4/448 |
| 3,847,313 | 11/1974 | Micallef | 222/538 |
| 3,874,381 | 4/1975 | Baum | 128/200.14 |
| 3,914,804 | 10/1975 | Schrader et al. | 4/420.2 |
| 4,000,742 | 1/1977 | DiGiacomo | 4/448 |
| 4,014,355 | 3/1977 | DiMatteo et al. | 4/420.2 |
| 4,069,519 | 1/1978 | Alexander | 4/447 |
| 4,069,520 | 1/1978 | Thomas | 4/446 |
| 4,178,931 | 12/1979 | Lind et al. | 4/448 |
| 4,206,520 | 6/1980 | Fulford | 4/665 |
| 4,234,127 | 11/1980 | Tada et al. | 222/533 |
| 4,236,655 | 12/1980 | Humphries | 222/530 X |
| 4,284,078 | 8/1981 | Pace | 604/150 |
| 4,422,189 | 12/1983 | Couvrette | 4/420.2 |
| 4,456,007 | 6/1984 | Nakao et al. | 128/200.21 |
| 4,510,630 | 4/1985 | Osgood | 4/443 |
| 4,516,697 | 5/1985 | Dreps et al. | 222/212 |
| 4,622,704 | 11/1986 | Chung | 4/443 |
| 4,706,848 | 11/1987 | D'Andrade | 222/79 |
| 4,803,974 | 2/1989 | Powell | 222/79 X |
| 4,890,340 | 1/1990 | Lovitt | 4/443 |

FOREIGN PATENT DOCUMENTS

| | | | |
|---|---|---|---|
| 477520 | 12/1929 | Fed. Rep. of Germany | 4/443 |
| 2387047 | 12/1978 | France | 604/151 |
| 4019 | of 1891 | United Kingdom | 4/447 |
| 1535794 | 12/1978 | United Kingdom | 4/448 |

OTHER PUBLICATIONS

Photocopy of Commercially Available Squirt Gun with Manual Pump and Bellows Style, Accordion Shaped Extensible/Retractable Nozzle manufactured by Lanard Toys in 1986.

*Primary Examiner*—Henry J. Recla
*Assistant Examiner*—Antoine Gamarra
*Attorney, Agent, or Firm*—Dickstein, Shapiro & Morin

[57] ABSTRACT

A self-contained hand-held bidet device, for providing lavaging action with portability and convenience. A somewhat pistol configuration housing contains a pump, controls and support for a retractable nozzle being sized and shaped to spray a stream of fluid from a reservoir mounted at one end of the housing. Lightweight construction and a collapsible reservoir facilitate convenient storage.

25 Claims, 4 Drawing Sheets

SELF-CONTAINED HAND-HELD BIDET

This is a continuation-in-part of pending application Ser. No. 249,053, filed Sept. 26, 1988 now U.S. Pat. No. 4,890,340, issued on Jan. 2, 1990 entitled "Self-Contained Hand-Held Bidet", which application has been allowed for issuance as a patent.

BACKGROUND OF THE INVENTION

1. Field of the Invention

The present invention relates in general to the field of hygienic devices and in particular to bidets. In that regard, the present invention is a portable, hand-held bidet for effective, hygienic cleaning with comfort and convenience.

2. Prior-Art Considerations

Traditionally, bidets perform various sanitary functions, and often accomplish this function to a degree superior to conventional sanitary devices. A conventional bidet is a rather large, non-portable fixture with attached plumbing to provide water supply and drainage.

The lavaging action of a conventional bidet is particularly quick, efficient and beneficial to persons who suffer from various medical problems, for example, hemorrhoids and genital or rectal infections. These problems are complicated by the fact that in many areas, bidets are not common. Thus, persons who would benefit from use of a conventional bidet may find their quality of life lessened by the inability to readily avail themselves of a bidet when the need arises.

In response to these problems, various attachment apparatuses have been proposed for mounting on a conventional flush toilet. Examples of such apparatuses are described in Kawai et al., U.S. Pat. No. 4,411,030; Matsui et al., U.S. Pat. No. 4,581,779; and Schrader et al., U.S. Pat. No. 3,914,804. Essentially, these structures are rather bulky, non-portable adaptor fixtures limited to use in one location.

The limited accessibility of non-portable and bulky conventional bidets or bidet attachment structures has put many bidet users at some inconvenience and prevented other potential users from obtaining the benefits of a bidet. Thus, the problems of inaccessibility, non-portability and the expense of conventional bidets restrict many persons from the benefits and convenience a bidet provides.

SUMMARY OF THE INVENTION

A substantial need exists for a relatively inexpensive, portable, easy-to-use bidet. In this regard, the present invention is directed to a selfcontained, hand-held bidet of relatively compact size, that is easy to use and provides the full benefits of a traditional bidet as well as other benefits. The present invention also provides the user with a measure of convenience not attendant traditional, conventional bidet apparatuses.

Specifically, the present invention comprises a self-contained hand-held bidet device for discharging a stream of fluid including: a rigid elongate slender housing having a first end and a second end adapted to be held in the hand of a user and defining an internal space between said first and second ends; a nozzle means defining an elongate conduit to carry and direct said stream of fluid; a fluid-seal means rigidly affixing said nozzle means to said first end of said housing, said nozzle means accordingly being mounted to retractably move between extended and retracted positions relative to said housing, said fluid-seal means and said nozzle means, when in the extended position, being sized and shaped to spray said stream of fluid away from said conduit in a longitudinal direction to impact a genital area of said user; a reservoir means for receiving said fluid, said reservoir means being attached to said second end of said housing; and pump means affixed to said housing for drawing fluid from said reservoir means and forcing a fluid stream through said fluid-seal means to emerge from said nozzle means.

In a disclosed embodiment, the pump means is an electric pump powered by a battery. In alternative embodiments, a manual pump is incorporated within the housing. Similarly, the conduit may have varying shapes and structures.

DESCRIPTION OF THE ILLUSTRATIVE EMBODIMENT

A detailed illustrative embodiment of the present invention is disclosed herein; however, it is merely representative recognizing that various electrical and mechanical components and various structural elements may be embodied in a wide variety of forms, some of which may be quite different from those specific structural and functional details disclosed herein. Consequently, the details disclosed herein are merely representative; yet in that regard they are deemed to afford the best embodiment for the purposes of disclosure to provide a basis for the claims herein which define the scope of the present invention.

Figure 1:
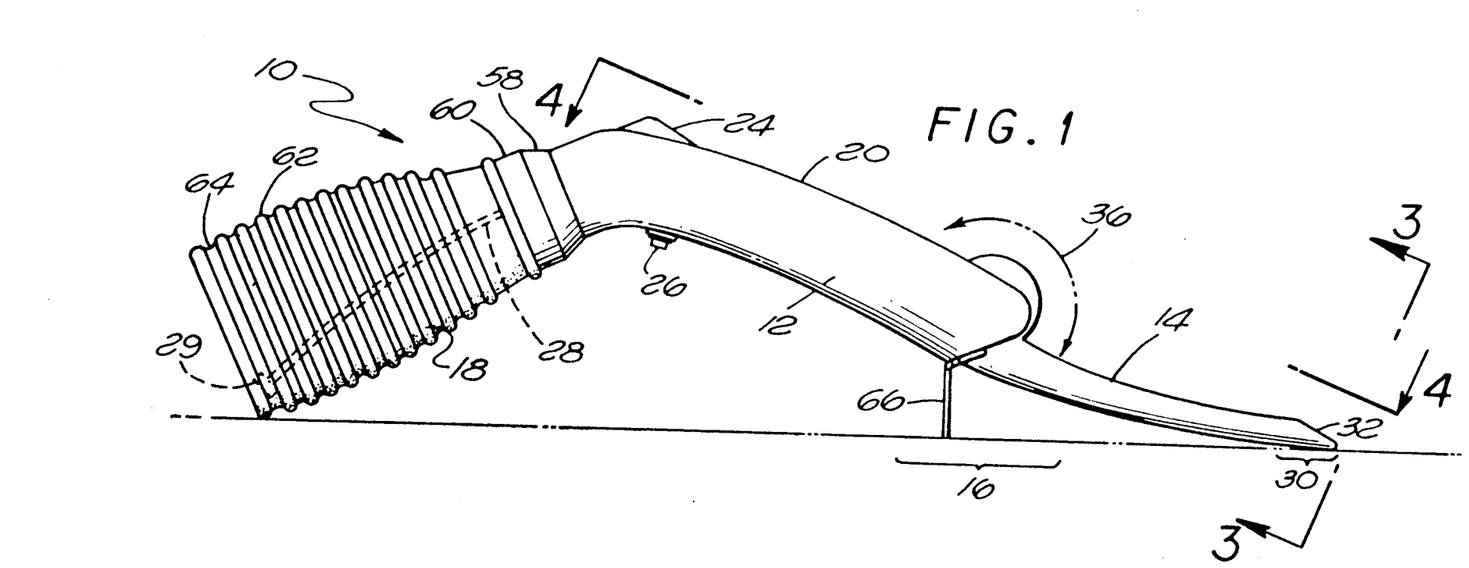
FIG. 1 is a side elevation view of a device of the present invention.
Figure 4:
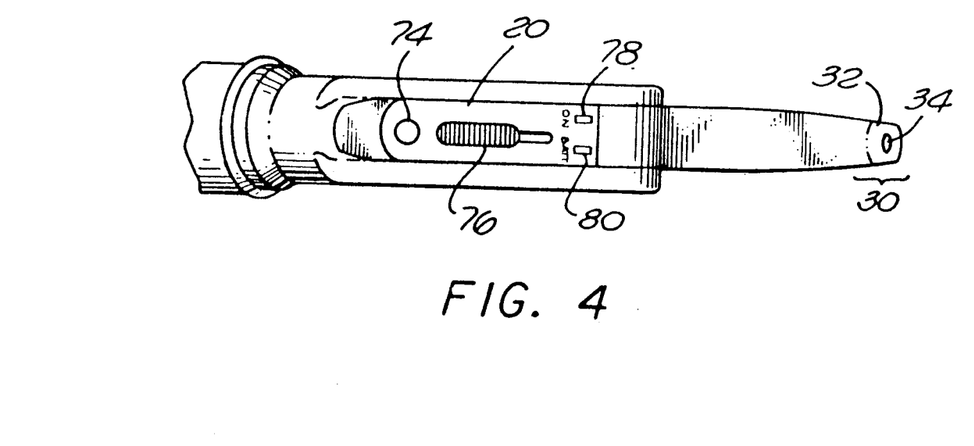
FIG. 4 is a partial top view taken along the line 4—4 of FIG. 1.

Referring initially to FIG. 1, there is illustrated a self-contained, hand-held bidet unit 10 in accordance with the present invention. A housing 12, made of plastic, fiberglass or lightweight metal and having a contoured, curved shape, is connected at one end to a conduit 14 by a pivot joint 16 and, at its other end, is coupled to a collapsible fluid reservoir 18 (fragment shown). The housing 12 is substantially cylindrical and curved throughout its axial length. The contoured, curved design of the housing 12 is designed to fit comfortably in either hand for easy manipulation and use of the unit 10. In this regard, the housing 12 has a flattened area defining a control panel 20 (FIG. 4). The panel 20 incorporates a contoured thumb rest 24 (FIG. 1) and various other operational controls, such as a soap/medication dispenser button 26, that protrude from the housing 12. The relatively compact size and contoured shape of the housing 12 and convenient positioning of both control panel 20 and soap/medication button 26 enable a user to operate the unit 10 with one hand.

As shown in FIG. 1, the curvature of the housing 12 is accentuated near the fluid reservoir 18. Consequently, the overall shape of the unit 10 is somewhat bent or angular and forms a somewhat pistol configuration. This design has several advantages. For example, when the unit 10 is operated in the position shown in FIG. 1, substantially all of the fluid contained within the fluid reservoir 18 can be drawn from it by means of an intake tube 28 shown in dotted lines. In this regard, the intake tube 28 has a screen filter 29 mounted to its intake end and extends to substantially the lowest region of the fluid reservoir 18 thereby maximizing the volume of fluid which may be drawn from the fluid reservoir 18.

Similarly, the unit's angular shape serves to balance the unit 10, thereby contributing to its easy manipulation and use. In this regard, the mass of filled-fluid reservoir 18 is somewhat counterbalanced by the mass of the housing 12, its components and the extended conduit 14. Accordingly, relatively little effort is required by the user to hold, operate and control the unit 10 in the operational position shown in FIG. 1.

The conduit 14, made of plastic or light metal, is mounted to be retractable in relation to the housing 12 and has a nozzle end 30 having a beveled surface 32 that defines a nozzle orifice 34 (FIG. 4) from which sprayed fluid exits the conduit 14. As shown by an arcuate arrow 36, (FIG. 1), a pivotal mounting of the conduit 14 allows it to be extended for spraying by pivoting it to an "open" position in which the unit 10 is operated (shown in FIG. 1). For storage, the conduit 14 is retracted by pivoting it to a "closed" position for convenient storage and portability of the unit 10. When not in use, the unit 10 may be rested on a surface supported by the fluid reservoir 18 and a protective plate that otherwise may be flipped closed to cover the end of the unit 10.

Figure 2:
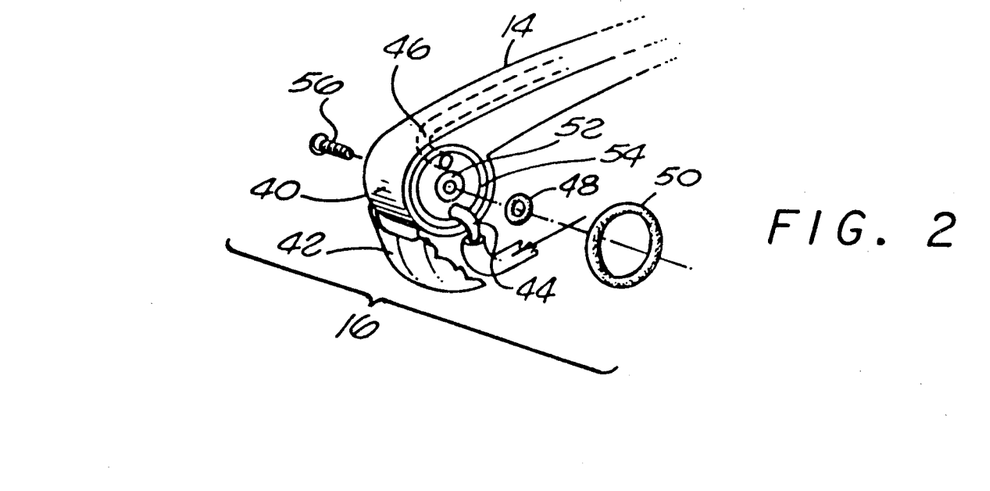
FIG. 2 is a fragmentary perspective view of a component of the device of FIG. 1.

Referring briefly to FIG. 2, the structure and operation of the pivot joint 16 (FIG. 1) is described. The ball and socket arrangement of the pivot joint 16 is comprised of a ball end 40 of the conduit 14 which is retractably mated into a "U" shaped socket structure 42 formed by the end of the housing 12. The end view illustrated in FIG. 3 more clearly shows the design of "U" shaped socket structure 42 into which the ball end 40 fits. The pivot joint 16 enables the conduit 14 to be easily extended and retracted. During operation of the unit 10, the pivot joint 16 maintains a substantially leak-tight seal between an output end of a output tube 44 located in the housing 12 and an intake end of a tubular bore 46 formed by the conduit 14. The leak-tight seal at the pivot joint 16 between these two tubular, fluid-bearing elements is accomplished by a system of concentrically seated O-rings 48 and 50 that rest in concentric channels 52 and 54 located on either or both the ball end 40 and the socket structure 42 and held in connective engagement via a screw 56.

The conduit 14 is rotatable around the axis centered at the screw 56 which serves as the axle for the pivot joint 16. As illustrated in FIG. 2, the pivot joint 16 is shown with the conduit 14 in the closed position with the output end of the output tube 44 and intake end of tubular bore 46 being unaligned which prevents fluid from traveling through the pivot joint 16. However, when the conduit 14 is pivoted into the open position, the output end of the output tube 44 is aligned with the intake end of the tubular bore 46 to provide a substantially continuous flow path for fluid pumped through the pivot joint 16.

Referring now to FIGS. 1 and 4, the slightly tapered, curved shape of the conduit 14 assists the user in directing a stream of fluid to the desired body area. The conduit 14 is relatively narrow and tapered from the ball end 40 to the nozzle end 30, as illustrated in FIG. 4, thus, it may be easily positioned between and slightly beneath the user's legs. Accordingly, this tapered design enables the unit 10 to be comfortably and easily used by many persons without significant effort.

Figure 3:
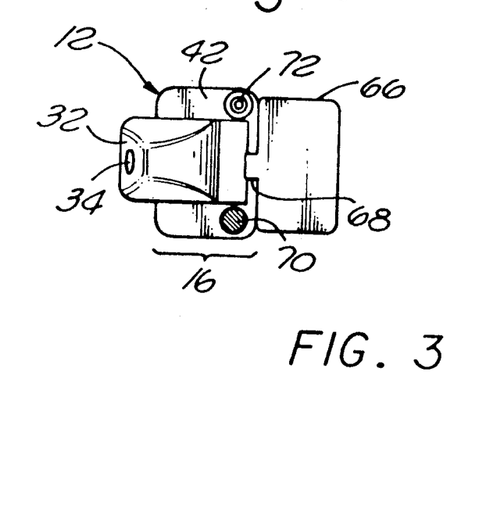
FIG. 3 is an end view taken along the line 3—3 of FIG. 2.

As illustrated in FIGS. 1 and 3, one end of the conduit 14 forms the nozzle end 30 which is designed to spray a single, coherent stream of fluid from the nozzle orifice 34 substantially orthogonal to the beveled surface 32. Accordingly, during use of the unit 10 the stream of fluid is directed to the desired area but sufficiently away from the conduit 14 and nozzle end 30 and substantially prevents soiling or contaminating material from the lavaged area from coming into contact with any part of the unit 10.

Referring again to FIG. 1, the coupling, made of light metal or plastic, couples the fluid reservoir 18 to the rest of the unit 10. The coupling has a truncated conical section 58 which forms a transitional structure between the housing 12 and a mating ring 60 which has a larger diameter. Both the inner wall (not shown) of the mating ring 60 and the outer wall of the mouth (not shown) of the fluid reservoir 18 are threaded so that the fluid reservoir 18 may be threadably secured.

The fluid reservoir 18, made of plastic or rubber, is collapsible for convenient storage and portability. In this regard, the fluid reservoir 18 incorporates an accordion-like design in its structure. Accordingly, alternating ridges 62 and valleys 64 extend circumferentially over a substantial portion of the fluid reservoir 18. In use, the fluid reservoir 18 may be expanded to its maximum fluid capacity. After use, the fluid reservoir 18 can be transformed into a compact, cylindrical shape by collapsing it thereby compressing the alternating ridges 62 and valleys 64 together in an accordion-like fashion. The ready and easy collapsibility of the fluid reservoir results in substantial space savings for storage and portability of the unit 10.

The fluid reservoir 18 is capable of holding enough fluid that the bidet may adequately lavage the desired area. In this regard, various volumetric capacities for the fluid reservoir 18 are possible. However, for use of unit 10 as a bidet, a volume of approximately one-half liter has been found to be sufficient for providing adequate lavaging. Additionally, it should be noted that the fluid reservoir 18, and indeed the unit 10, may be used with a wide variety of fluids, including water or medicated solutions, depending on the user's needs.

Referring to FIG. 3, when the conduit 14 is extended, a protective plate 66 flips down via a springloaded hinge 68 to provide a support for resting the unit 10 on a surface and, at the same time, to provide access to other features of the unit 10. When the conduit 14 is retracted, the protective plate 66 protects the end of the unit 10 and is held closed by the spring-loaded hinge 68 to prevent it from opening accidentally. Flipping down plate 66 exposes a soap/medicant reservoir access plug 70 and a battery recharging socket 72. The protective plate 66 may be opened independently of extending the conduit 14. This feature allows soap or medication to be added to the unit 10 by removing access plug 70 and filling a reservoir 100 without extending the conduit 14. Similarly, recharging of the unit's batteries may be accomplished by attaching an appropriate adaptor/recharger unit to the battery recharging socket 72.

Referring now to FIG. 4, some discussion of the control features of the bidet are appropriate. FIG. 4 is a partial top view of the device in FIG. 1 illustrating an exemplary control panel 20 of the unit 10. The control panel 20 comprises a flattened upper surface of the housing 12 which mates with a conduit surface when the conduit 14 is retracted. To access the control panel 20 and operate the unit 10, the user extends the conduit 14 thereby exposing the control panel 20. Located on the control panel 20 is an "on/off" switch 74, a rheostat 76, an "on/off" indicator light 78 and a "battery low" indicator light 80. The "on/off" switch 74 enables the user to switch the unit 10 on or off. When the unit 10 is on, the "on/off" indicator light 78 is illuminated to provide the user with a visual indication. The rheostat 76 enables the user to vary the pressure of the stream of fluid by controlling the output of a pump located within the housing 12. If the unit 10 needs recharging or needs a new battery, then the "battery low" indicator light 80 is illuminated when the unit 10 is activated.

Figure 5:
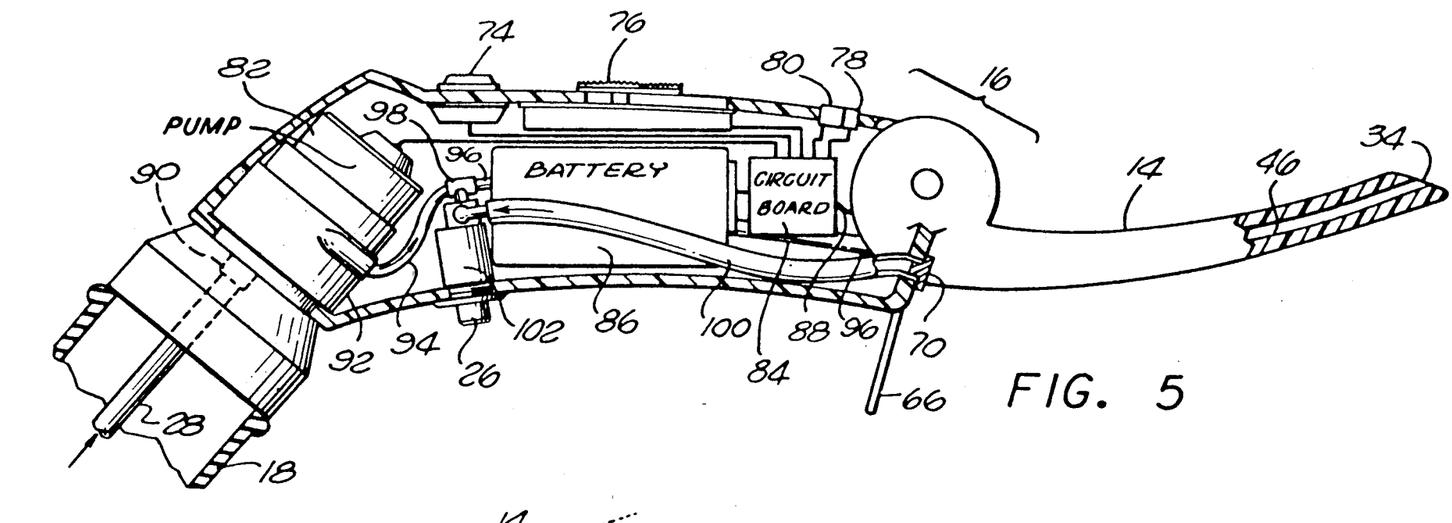
FIG. 5 is vertical cross-sectional, view of the device in FIG. 1.

Referring now to FIG. 5, further specifics regarding the structure and operation of a battery-powered electric pump bidet will be described in more detail. Positioned in the housing 12 are, among other things, an electric system comprising the "on/off" switch 74, the rheostat switch 76, the "on/off" indicator light 78, the "battery low" indicator light 80 and a pump 82 each of which is wired to a circuit board 84 which is in turn wired to a battery 86 for powering the unit 10. If a rechargeable battery is utilized to power the unit 10, then the circuit board 84 is additionally wired to the battery recharging socket 72 (FIG. 3) via a connection 88.

In operation, the unit 10 is switched on by depressing the "on/off" switch 74 which energizes unit 10, both illuminating the "on/off" indicator light 78 and energizing the pump 82. When the user moves the rheostat 76, the pump 82 is activated to operate at the speed selected by the user via the rheostat 76. Accordingly, the pump 82 draws fluid from the fluid reservoir 18 via the intake tube 28 and into the pump 82 through a pump intake port 90. The fluid is then driven from the pump 82 through a pump output port 92 through an output tube 94 to a secondary output tube 96 via a "T" junction 98. The secondary output tube 96 supplies fluid to the conduit 14 through the pivot joint 16. The fluid travels through the tubular bore 46 of the conduit 14 and exits the unit 10 through the nozzle orifice 34 as a spray or stream for lavaging.

To use the battery-powered electric pump bidet, the user first removes and fills the fluid reservoir 18 with fluid. Lukewarm water is usually preferred by most bidet users, but other fluids may be used depending on the user's needs. Once filled, the fluid reservoir 18 is reattached via a mating ring 60 to the housing 12. The user then extends the conduit 14 to move the nozzle end 30 to a spraying position and to expose the control panel 20. Subsequently, the user assumes a comfortable position and positions the unit 10 so that the spray from the nozzle orifice 34 will impact on the desired body area.

When ready, the user activates the unit 10 by depressing the "on/off" switch 74 to the "on" position which energizes the unit 10 as indicated by illuminating the "on/off" indicator light 78. The user then slides the rheostat 76 to adjust the pressure of the spray and lavages the desired body area until it is cleansed or until the fluid supply in the fluid reservoir 18 is exhausted. As noted earlier, the design of the unit 10 substantially reduces the opportunity for contamination of the unit 10 by contact with contaminated matter or fluid from the sprayed area. Once finished, the user depresses the "on/off" switch 74 to return it to the off position thereby deactivating the unit 10 and extinguishing the "on/off" indicator light 78.

If further lavaging is desired, the fluid reservoir 18 may be removed, refilled and reattached and the unit 10 reactivated. This cycle may be repeated as many times as desired. However, for normal use, the volume of fluid in fluid reservoir 18 is usually sufficient to provide adequate cleaning action within one cycle. When the user finishes with their ablutions, they deactivate the unit 10 and prepare it for storage by retracting the conduit 14 and flipping protective plate 66 into the up position to cover the end of the housing 12. The fluid reservoir 18 may be removed, rinsed, dried and collapsed and the whole unit 10 stored conveniently in a purse or handy carrying case for easy portability until needed again.

Various modifications of the bidet may enhance its utility and effectiveness. Some modifications are shown in other figures and will now be considered. Note that elements similar to those described above bear similar reference numerals. Referring to FIG. 5, the bidet may be used to apply soap or medication together with the stream of fluid to enhance the cleansing action and medical uses of the unit 10. In this regard, the soap/medication reservoir 100 and a dispenser 102 are provided for injecting soap or medication into the stream of fluid during the bidet's operation. To utilize this feature, the user simply removes the access plug 70 from the end of the reservoir 100 and fills it with soap or medication and reseals the reservoir 100 by replacing access plug 70. The user then activates the bidet 10 as described earlier and, while lavaging, depresses the soap/medication button 26 (FIG. 1) on the dispenser 102 thereby causing a small amount of soap or medication to be injected into the stream of fluid at the "T" junction 98. Repeated depressing of the button 26 enables the unit 10 to deliver several applications of soap or medicated solution onto the desired body area.

Figures 6, 7:
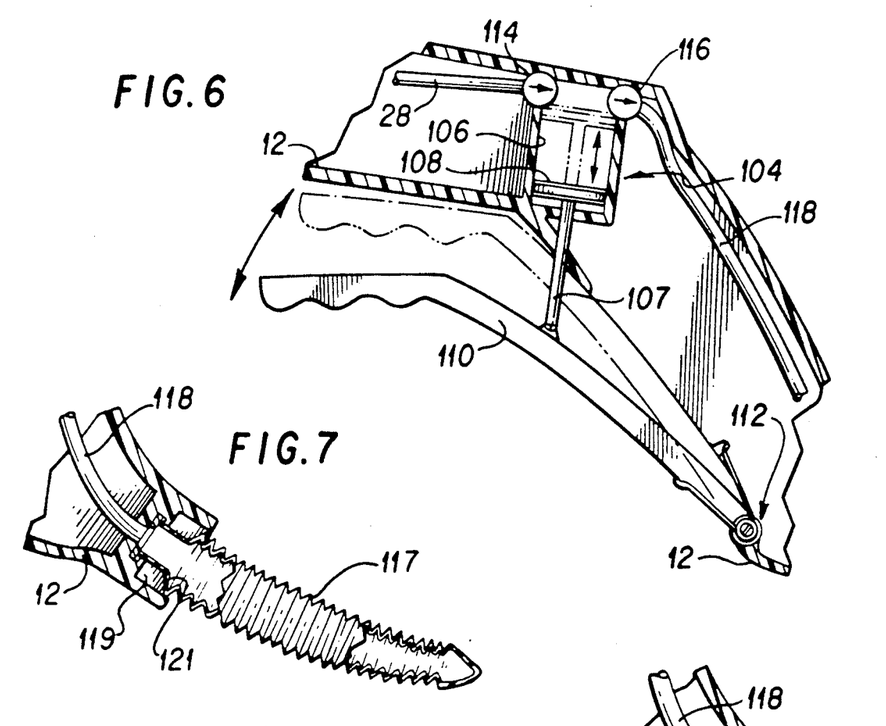
FIG. 6 is a fragmentary view similar to FIG. 5 showing elements of an alternative embodiment.
FIG. 7 is a fragmentary view similar to FIG. 6 showing elements of an alternative embodiment incorporating a telescopic conduit.

FIG. 6 shows an alternative embodiment of the bidet utilizing a manual pump. In the unit of FIG. 6, the pump 82 of FIG. 5 is replaced by a manual pump 104. A cylinder 106 receives a piston 108 to draw fluid from the fluid reservoir 18. The piston 108 of the manual pump 104 is actuated through a connecting rod 107 by a reciprocating lever 110. The lever 110 is elongate and formed to align with the pistol configuration of the housing. Notches protrude from the downward side of the free end of the lever 110 to allow the user's hand to grip the lever and urge the lever toward the housing.

The lever 110 is pivotally attached to the housing 12 near the forward end of the housing 12 by a spring-loaded hinge 112. The hinge 112 urges the lever 110 away from the housing 12, thus moving the piston 108 downward within the cylinder 106.

The down stroke of the piston 108 draws fluid from the fluid reservoir 18 into the cylinder 106 through the intake tube 28. A check valve 114 allows fluid to enter the cylinder 106 and prevents fluid from returning to the fluid reservoir 18 (FIG. 1).

When the lever 110 is gripped and forcefully raised to a position adjacent to the housing 12, the spring-loaded hinge 112 is cocked and the piston 108 forces fluid through a check valve 116. Note that fluid is prevented from reentering the intake tube 28 by the check valve 114. However, the check valve 116 allows the fluid to flow out of the cylinder 106 and into an output tube 118 for discharge as a spray or stream.

Figures 7A, 9:
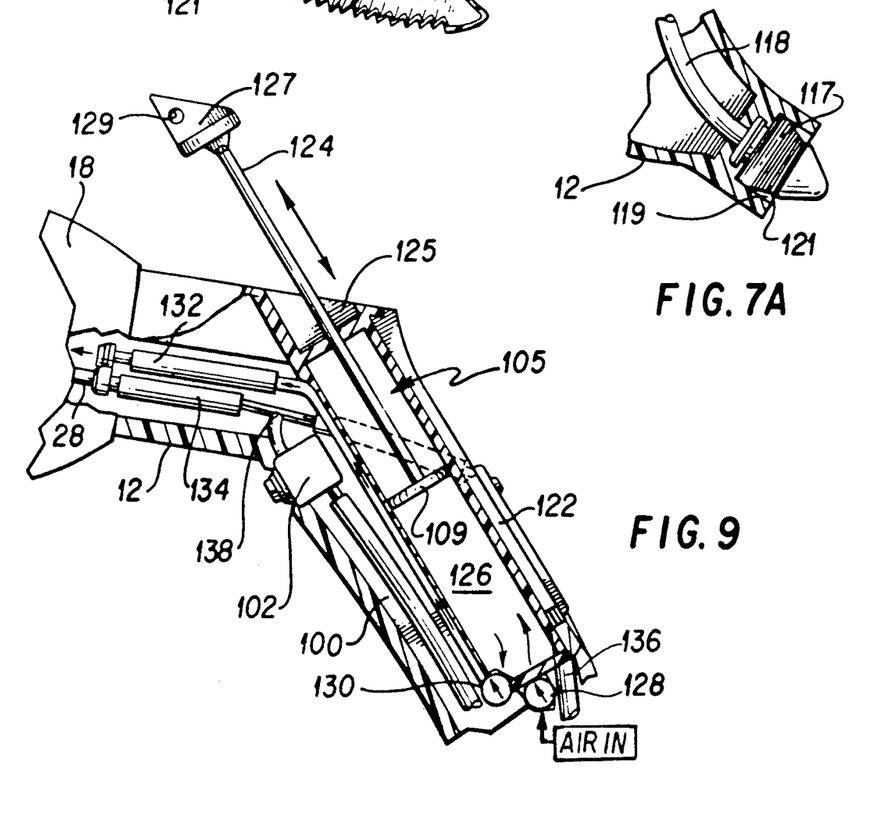
FIG. 7A is a fragmentary view similar to FIG. 7 showing the telescopic conduit stored in a retracted position within the bidet housing.
FIG. 9 is a fragmentary view similar to FIG. 1 showing elements of an alternative embodiment.

FIG. 7 illustrates an alternative structure for the conduit 14 and the housing 12. A conduit 117 incorporates a flexible accordion-like design of tubular configuration. The housing 12 defines a cylindrical well 119 at its forward end. When the bidet is not in use, as illustrated in FIG. 7A, the conduit 117 may be collapsed and accordingly retracted into a compact, cylindrical shape and stored within the well 119. The housing 12 forms a circular rim 121 which surrounds the conduit 117 as the conduit exits the housing. When the conduit 117 is retracted, the rim 121 retains the conduit within the well 119.

Figures 8, 10:
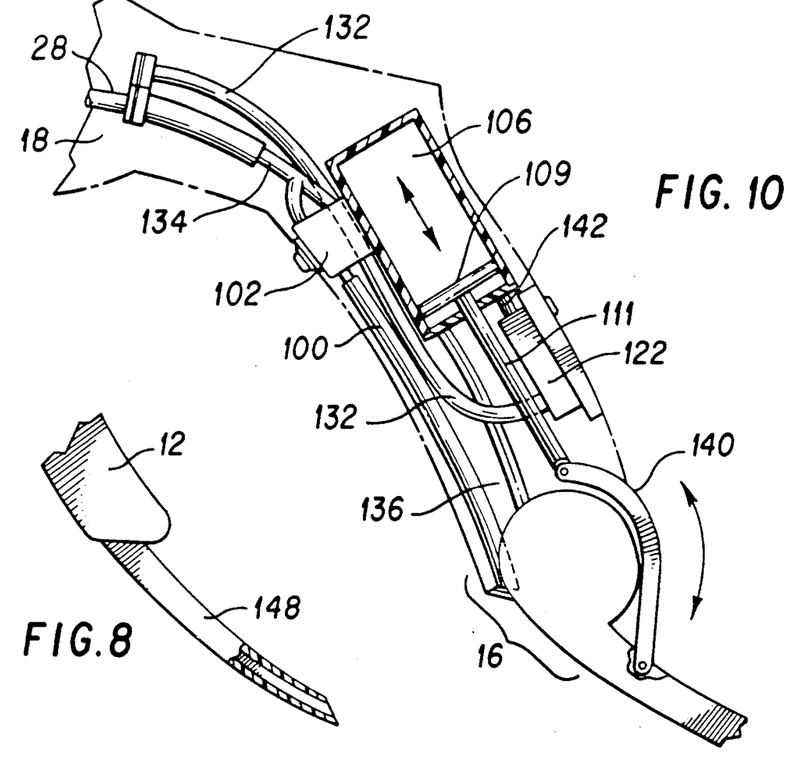
FIG. 8 is a fragmentary view similar to FIG. 7 showing elements of an alternative embodiment incorporating a flexible conduit.
FIG. 10 is a fragmentary view similar to FIG. 1 showing elements of an alternative embodiment.
Figure 8A:
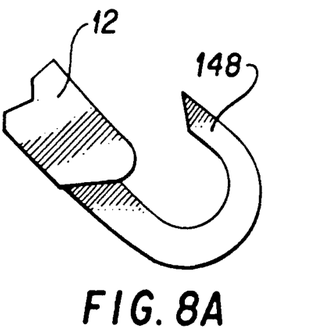
FIG. 8A is a fragmentary view similar to FIG. 8 showing the flexible conduit in a bent position.

The conduit may also be embodied in a gooseneck structure as illustrated in FIG. 8. A conduit 148 is constructed of a flexible plastic or metal capable of being forcefully distorted to extended and retracted positions. In a retracted position, the conduit 148, as illustrated in FIG. 8A, retains a shape wherein the conduit hooks backward and over the housing 12.

FIG. 9 shows another alternative embodiment of the hand-held bidet utilizing a pneumatic hand pump and a plunger. In this embodiment, a manual pump 105 is combined with a variable pressure regulator 122 to introduce pressurized air into the fluid reservoir 18 thus forcing fluid out of the fluid reservoir 18. A plunger 124 actuates a piston 109 within the manual pump 105. When not in use, the plunger 124 is depressed toward the housing 12 to rest within a well 125. A wedge-shaped grip 127 located on the upper end of the plunger 124 defines a hole 129. The grip 127 is flush with the housing 12 when the plunger is fully depressed. However, the hole 129 allows the user to grasp the grip as it is stored within the well and pull the plunger 124 away from the housing 12.

When the plunger is pulled away from the housing 12, air enters a manual pump cylinder 126 through a check valve 128. Air is forced from the manual pump cylinder 126 when the piston 109 is moved downward by depressing the plunger 124 toward the housing 12. The air exits the chamber through a check valve 130 and enters a pressure supply tube 132 which in turn passes the air to the fluid reservoir 18. The introduction of air under pressure into the fluid reservoir 18 forces fluid into the intake tube 28. The fluid then flows through a fluid supply tube 134 to a conduit supply tube 136 via a "T" junction 138. The conduit supply tube 136 passes fluid to the conduit 14 (FIG. 1) and the fluid exits the bidet through the nozzle orifice 34 (not shown).

FIG. 10 illustrates another alternative embodiment incorporating a manual pump somewhat as described with reference to FIG. 9. In FIG. 10, a connecting rod 111 is linked from the piston 109 to the conduit 14 by a pivot linkage 140. As the conduit 14 is pivotally moved about the joint 16, the linkage 140 actuates the piston 109 within the cylinder 126 and forces air into an output tube 142. The air then enters the variable pressure regulator 122 and passes from there into the pressure supply tube 132. Air exits the pressure supply tube 132 and enters the fluid reservoir 18. The resulting build up of air pressure in the fluid reservoir 18 causes fluid to enter the intake tube 28 and flow into the fluid supply tube 134. The fluid supply tube 134 transmits the fluid to the conduit supply tube 136 and then the fluid passes to the conduit (not shown).

Figure 11:
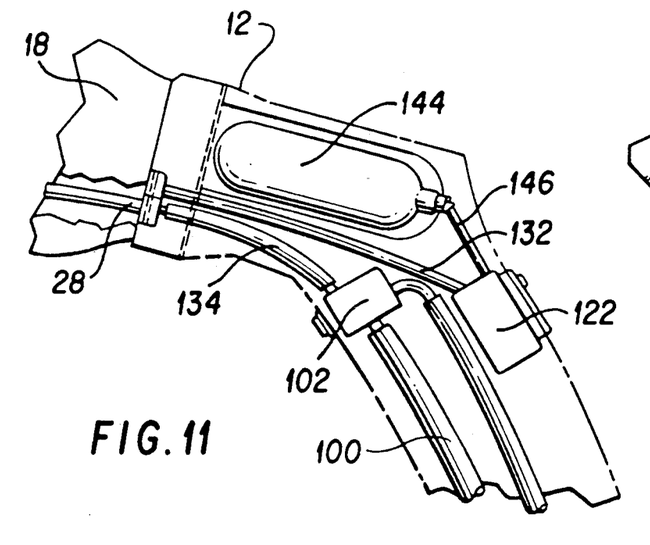
FIG. 11 is a fraqmentary view similar to FIG. 1 showing elements of an alternative embodiment.

FIG. 11 illustrates another embodiment of the hand-held bidet utilizing a carbon dioxide cartridge for pressure. In this embodiment, a carbon dioxide cartridge 144 is mounted in the housing 12. A cartridge output tube 146 transmits carbon dioxide from the carbon dioxide cartridge 144 to the variable pressure regulator 122. Once the variable pressure regulator 122 controls the amount of carbon dioxide exiting the carbon dioxide cartridge 144, the carbon dioxide enters the pressure supply tube 132 and passes to the fluid reservoir 18. The introduction of pressurized carbon dioxide to the fluid reservoir 18 forces fluid into the intake tube 28 and then into the fluid supply tube 134.

In FIGS. 8 through 10, a soap/medication reservoir may be placed between the fluid supply tube 134 and the conduit supply tube 136. Similar to FIG. 5, the soap/medication reservoir 100 and the dispenser 102 may be provided for injecting soap or medication into the stream of fluid during the day's operation. The access plug 70 is used to fill the soap/medication reservoir 100, and the button 26 is depressed to inject soap or medication into the fluid stream.

The portability of the bidet and its compact design with a retractable discharge conduit enable a user to obtain the traditional benefits of a bidet almost anywhere, whenever the need for use arises. That is, a collapsible reservoir and the retractably mounted conduit contribute to the compact size of the bidet, enabling it to be carried in a purse or in its own convenient carrying case. Because the unit may be selfcontained, its convenience is further enhanced. In this regard, the bidet provides its own fluid source, i.e. fluid reservoir 18 (FIG. 1) and its own power source, i.e. battery 86 (FIG. 4) or carbon dioxide cartridge 144 (FIG. 11), or a manual pump (FIGS. 6, 8 and 9).

In view of the above description of the preferred embodiments, it will be apparent that the present invention is capable of economical implementation in a variety of shapes and functional designs to accomplish an effective, economical and easy-to-use bidet. Such modifications may include varying the reservoir capacity, increasing or decreasing the pump rate or the type of pump used, and varying the spray patterns produced by the nozzle to effectively address the needs of the user and contemplated use of the present invention. Consequently, the scope of the present invention hereof is deemed to be appropriately determined by the claims as set forth below.

What is claimed is:

1. A self-contained hand-held bidet device for discharing a stream of fluid comprising:
   a rigid elongate slender housing having a longitudinal axis with a first end and an opposite second end along said axis and adapted to be held in the hand of a user and defining an internal space between said first and second ends;

a nozzle means defining a rigid elongate conduit to carry and direct said stream of fluid;

a fluid-seal means rigidly affixing the first end of said nozzle means to said first end of said housing, said nozzle means accordingly being mounted to retractably move between an extended position where said nozzle means extends outwardly from said housing and a retracted position where said nozzle means extends alongside said housing toward said second end, said fluid-seal means and said nozzle means, when in the extended position, being sized and shaped to spray said stream of fluid away from said conduit in a longitudinal direction to impact a genital area of said user;

a self-contained reservoir means for receiving said fluid, said reservoir means being attached to said housing to be carried with said housing;

pump means affixed to said housing for drawing fluid from said reservoir means and forcing a fluid stream through said fluid-seal means to emerge from said nozzle means; and a battery contained in said housing for powering said pump.

2. A bidet device according to claim 1 wherein:
said nozzle means comprise an elongate arcuate conduit; and
said housing defines an elongate surface to mate with a surface of said conduit in said retracted position.

3. A bidet device according to claim 1 wherein said pump means comprise:
an electric pump;
a control circuit; and
a switch.

4. A bidet device according to claim 1 wherein said pump means comprise:
a cylinder;
a piston matingly received within said cylinder;
at least one check valve; and
a lever connected to said piston and connected to said housing.

5. A bidet device according to claim 4 wherein said lever comprises:
an elongate slender lever having a first and a second surface;
said first surface adapted to mate with said housing; and
said second surface defining at least one indentation.

6. A bidet device according to claim 5 further comprising:
a spring loaded hinge connecting said lever to said housing.

7. A bidet device according to claim 1 wherein:
said reservoir means comprises an accordion-like structure collapsible to a reduced size.

8. A bidet device according to claim 1 wherein said reservoir means comprise:
a removable attached structure removable from said housing to be filled with fluid.

9. A bidet device according to claim 1 wherein:
said reservoir means is expandable to accommodate substantially one-half liter of fluid.

10. A bidet device according to claim 1 further comprising:
a soap/medication chamber; and
means for connecting said chamber to said pump means to inject soap/medication.

11. A bidet device according to claim 1 wherein:
said fluid-seal means include a cylindrical structure defining an axially parallel passage for said fluid.

12. A bidet device according to claim 1 wherein:
said housing defines a handle for said device.

13. The portable, hand-held bidet of claim 1, wherein said battery is rechargeable.

14. The portable, hand-held bidet of claim 1, further including a control circuit and switch means connected between said battery and said pump.

15. A self-contained hand-held bidet device for discharging a stream of fluid comprising:
a rigid elongate slender housing having a longitudinal axis with a first end and an opposite second end along said axis and adapted to be held in the hand of a user and defining an internal space between said first and second ends;

a nozzle means defining an elongate conduit to carry and direct said stream of fluid;

a fluid-seal means rigidly affixing a first end of said nozzle means to said first end of said housing, said nozzle means accordingly being mounted to retractably move between an extended and a retracted position to said housing said fluid-seal means and said nozzle means, when in the extended position, being sized and shaped to spray said stream of fluid away from said conduit in a longitudinal direction to impact a genital area of said user;

said fluid seal means includes a cylindrical structure with two axially parallel bores wherein when said nozzle means is in said retracted position said bores are misaligned to prevent fluid flow and when said nozzle means is in said extended position said bores are aligned to allow fluid flow;

a self contained reservoir means for receiving said fluid, said reservoir means being attached to said housing to be carried with said housing; and pump means affixed to said housing for drawing fluid from said reservoir means and forcing a fluid stream through said fluid-seal means to emerge from said nozzle means.

16. A bidet device according to claim 15 wherein said pump means comprise:
a manual pump.

17. A bidet device according to claim 16 wherein said manual pump comprises:
a cylinder;
a piston matingly received within said cylinder; and
a plunger connected to the piston.

18. A bidet device according to claim 17, wherein said manual pump further comprises:
a pressure regulator.

19. A bidet device according to claim 17 wherein said manual pump further comprises:
a connecting rod linked between said piston and said nozzle means; and
said fluid-seal means mounts said nozzle means to pivot between said extended and retracted positions.

20. A bidet device according to claim 15 wherein said pump means comprise:
a carbon dioxide cartridge; and
a switch.

21. A bidet device according to claim 20 wherein said pump means further comprise:
a pressure regulator.

22. The portable, hand-held bidet of claim 15, wherein said reservoir means comprises a removably threadably attached structure, removable from said housing to be filled with fluid.

23. The portable, hand-held bidet of claim 15, wherein said reservoir means is expandable to accommodate substantially one-half liter of fluid.

24. The portable, hand-held bidet of claim 15, further including a soap/medication chamber and means for connecting said chamber to said pump to inject soap/medication into said fluid spray.

25. The portable, hand-held bidet of claim 15, wherein said housing defines a handle for said bidet.

* * * * *